(12) United States Patent
Kwon et al.

(10) Patent No.: US 9,617,475 B1
(45) Date of Patent: Apr. 11, 2017

(54) LIQUID CRYSTAL COMPOSITION AND LIQUID CRYSTAL DISPLAY COMPRISING THE SAME

(71) Applicant: Samsung Display Co. Ltd., Yongin, Gyeonggi-do (KR)

(72) Inventors: Sun Young Kwon, Seoul (KR); Keun Chan Oh, Cheonan-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/074,391

(22) Filed: Mar. 18, 2016

(30) Foreign Application Priority Data

Oct. 7, 2015 (KR) .......................... 10-2015-0140867

(51) Int. Cl.
| G02F 1/1333 | (2006.01) |
| C09K 19/30 | (2006.01) |
| C07C 43/225 | (2006.01) |
| C07C 25/13 | (2006.01) |
| C07C 25/24 | (2006.01) |
| G02F 1/1368 | (2006.01) |

(52) U.S. Cl.
CPC .......... C09K 19/3003 (2013.01); C07C 25/13 (2013.01); C07C 25/24 (2013.01); C07C 43/225 (2013.01); G02F 1/1368 (2013.01); C07C 2101/14 (2013.01); C09K 2019/301 (2013.01); C09K 2019/3004 (2013.01); C09K 2019/3009 (2013.01); C09K 2019/3016 (2013.01)

(58) Field of Classification Search
CPC ........ C09K 19/3003; C09K 2019/3004; C09K 2019/3009; C09K 2019/301; C09K 2019/3016; C07C 19/3003; C07C 25/13; C07C 25/24; C07C 2101/14; G02F 1/1333; G02F 1/1368
USPC .......................... 252/299.01, 299.6; 349/182
See application file for complete search history.

(56) References Cited

U.S. PATENT DOCUMENTS 5,965,060 A 10/1999 Tarumi et al.

*Primary Examiner* — Geraldina Visconti
(74) *Attorney, Agent, or Firm* — Cantor Colburn LLP

(57) ABSTRACT

A liquid crystal composition includes at least one first compound represented by Formula I:

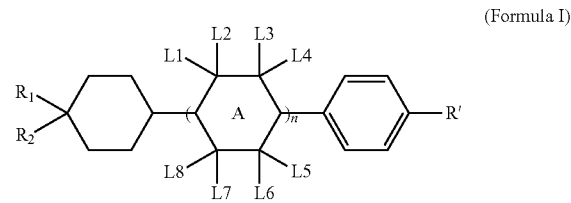

(Formula I)

wherein each of L1 to L8 are independently a hydrogen or a fluorine;

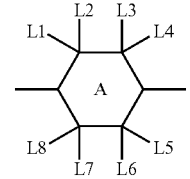

is a cyclohexyl group, a phenyl group, tetrahydropyran, 1,3-dioxane, a fluorocyclohexyl group, a fluorophenyl group, fluorotetrahydropyran, or fluoro-1,3-dioxane; n is 0 to 2, and when n=2, each

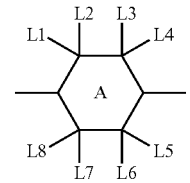

is independently a cyclohexyl group, a phenyl group, tetrahydropyran, 1,3-dioxane, a fluorocyclohexyl group, a fluorophenyl group, fluorotetrahydropyran, or fluoro-1,3-dioxane; each of $R_1$ and $R_2$ is independently a $C_{1-2}$ alkyl group; and R' is hydrogen, a $C_{1-5}$ alkyl group, a $C_{2-5}$ alkenyl group, or a $C_{1-5}$ alkoxy group.

8 Claims, 2 Drawing Sheets

LIQUID CRYSTAL COMPOSITION AND LIQUID CRYSTAL DISPLAY COMPRISING THE SAME

This application claims priority to Korean Patent Application No. 10-2015-0140867, filed on Oct. 7, 2015, and all the benefits accruing therefrom under 35 U.S.C. §119, the content of which in its entirety is herein incorporated by reference.

BACKGROUND

1. Field of the Invention

The invention relates to a liquid crystal composition and a liquid crystal display (LCD) comprising the same.

2. Description of the Related Art

A liquid crystal display (LCD), is one of the most widely-used flat panel displays. The LCD includes two substrates on which field-generating electrodes such as pixel electrodes and a common electrode are formed and a liquid crystal layer interposed between the two substrates.

As the field of application of LCDs has widened, improvements in the properties of LCDs, such as response speed, contrast ratio, and driving voltage characteristics, have improved. To improve the properties of LCDs, it is desirable for the a liquid crystal compound contained in a liquid crystal composition to have low rotational viscosity, high chemical and physical stability, a high liquid phase-to-isotrophic phase transition temperature, a low liquid-phase lower limit temperature, and an appropriate elastic modulus. In particular, a low-rotational viscosity liquid crystal material is desired to provide high-speed response characteristics.

SUMMARY

Exemplary embodiments of the invention provide a liquid crystal composition comprising a novel low-viscosity polar liquid crystal compound.

Exemplary embodiments of the invention also provide a liquid crystal display comprising a liquid crystal layer comprising a novel low-viscosity polar liquid crystal compound.

According to an exemplary embodiment, a liquid crystal composition includes a novel low-viscosity polar liquid crystal compound. In another exemplary embodiment, an LCD including the liquid crystal composition is provided.

According to an exemplary embodiment, a liquid crystal composition includes at least one first compound represented by Formula I.

According to another exemplary embodiment, a liquid crystal display (LCD) includes a first display substrate including thin-film transistors (TFTs), a second display substrate facing the first display substrate and a liquid crystal layer comprising at least one first compound represented by

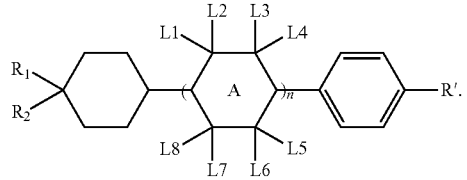

Formula I

In Formula I, each of L1 to L8 is a hydrogen or a fluorine;

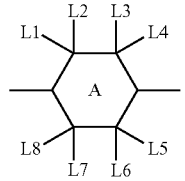

(Formula I)

is a cyclohexyl group, a phenyl group, tetrahydropyran, 1,3-dioxane, a fluorocyclohexyl group, a fluorophenyl group, fluorotetrahydropyran, or fluoro-1,3-dioxane; n is 0 to 2, and when n=2, each

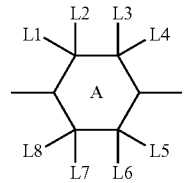

is independently a cyclohexyl group, a phenyl group, tetrahydropyran, 1,3-dioxane, a fluorocyclohexyl group, a fluorophenyl group, fluorotetrahydropyran, or fluoro-1,3-dioxane; each of $R_1$ and $R_2$ is independently a $C_{1-2}$ alkyl group; and R' is hydrogen, a $C_{1-5}$ alkyl group, a $C_{2-5}$ alkenyl group, or a $C_{1-5}$ alkoxy group.

Other features and exemplary embodiments will be apparent from the following detailed description, the drawings, and the claims.

BRIEF DESCRIPTION OF THE DRAWINGS

A more complete appreciation of the present disclosure, and many of the attendant advantages thereof, will be readily apparent when the following detailed description is considered in conjunction with the accompanying drawings, in which.

DETAILED DESCRIPTION

Figure 1:
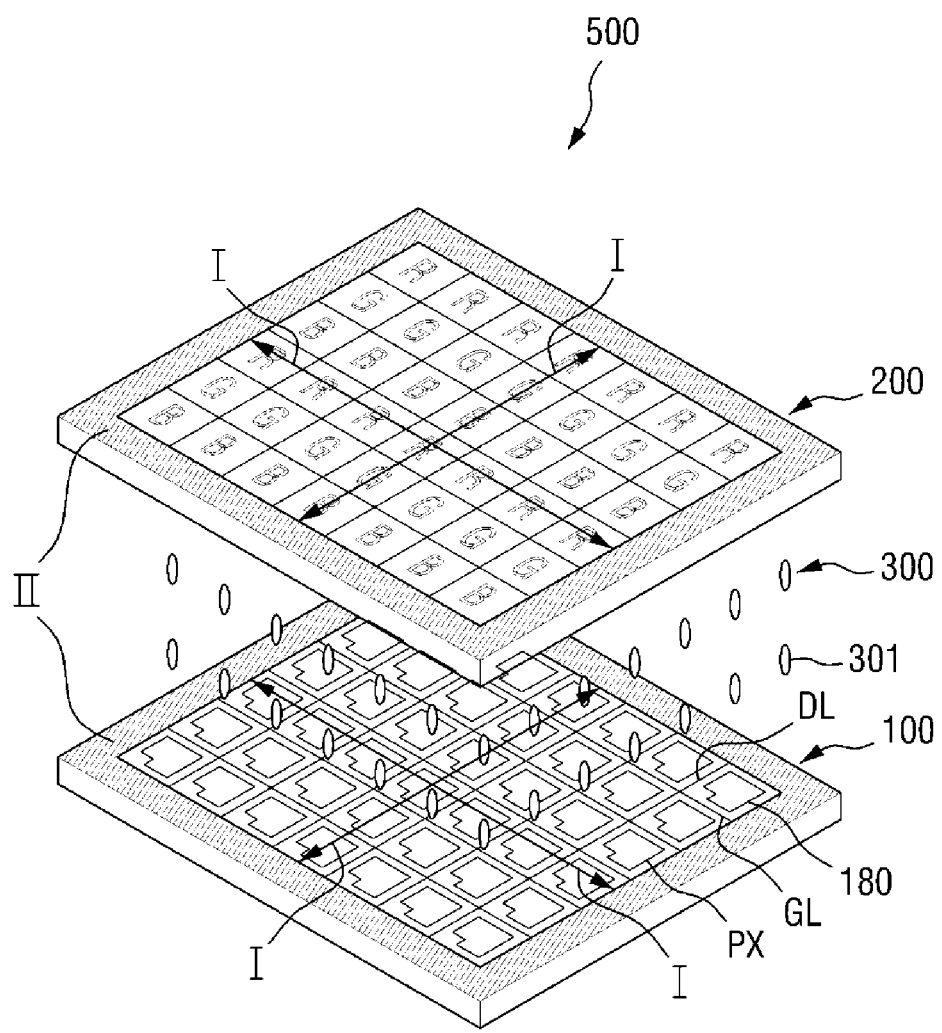
FIG. 1 is a schematic exploded perspective view of an exemplary embodiment of a liquid crystal display (LCD)

Features of the inventive concept and methods of accomplishing the same may be understood more readily by referencing the following detailed description and the accompanying drawings. The inventive concept may, however, be embodied in many different forms and are not limited to the embodiments set forth herein. Rather, these embodiments are provided to help illustrate the scope of the invention to those of ordinary skill in the art.

In the drawings, the thickness of layers and regions are exaggerated for clarity. It will be understood that when an element or layer is referred to as being "on", "connected to" or "coupled to" another element or layer, the element or layer may be directly on, connected or coupled to another element or layer, or intervening elements or layers. In contrast, when an element is referred to as being "directly on", "directly connected to" or "directly coupled to" another element or layer, there are no intervening elements or layers present. As used herein, connected may refer to elements being physically, electrically and/or fluidly connected to each other.

Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections are not limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

Spatially related terms, such as "below", "lower", "under", "above", "upper" and the like, may be used herein for ease of description to describe the relationship of one element or feature to another element(s) or feature(s) as illustrated in the figures. It will be understood that the spatially related terms are intended to encompass different orientations of the device in use or operation, in addition to the orientation depicted in the figures. For example, if the device in the figures is turned over, elements described as "below" or "beneath" relative to other elements or features would then be oriented "above" relative to the other elements or features. Thus, the exemplary term "below" can encompass both an orientation of above and below. The device may be otherwise oriented (rotated 90 degrees or at other orientations) and the spatially related descriptors used herein may be interpreted accordingly.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises", "comprising", "includes" and/or "including", when used in this specification, specify the presence of stated features, integers, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The term "$C_{A-B}$", as used herein, refers to a carbon number of A to B. For example, the term "$C_{1-5}$" refers to a carbon number of one to five.

Figure 2:
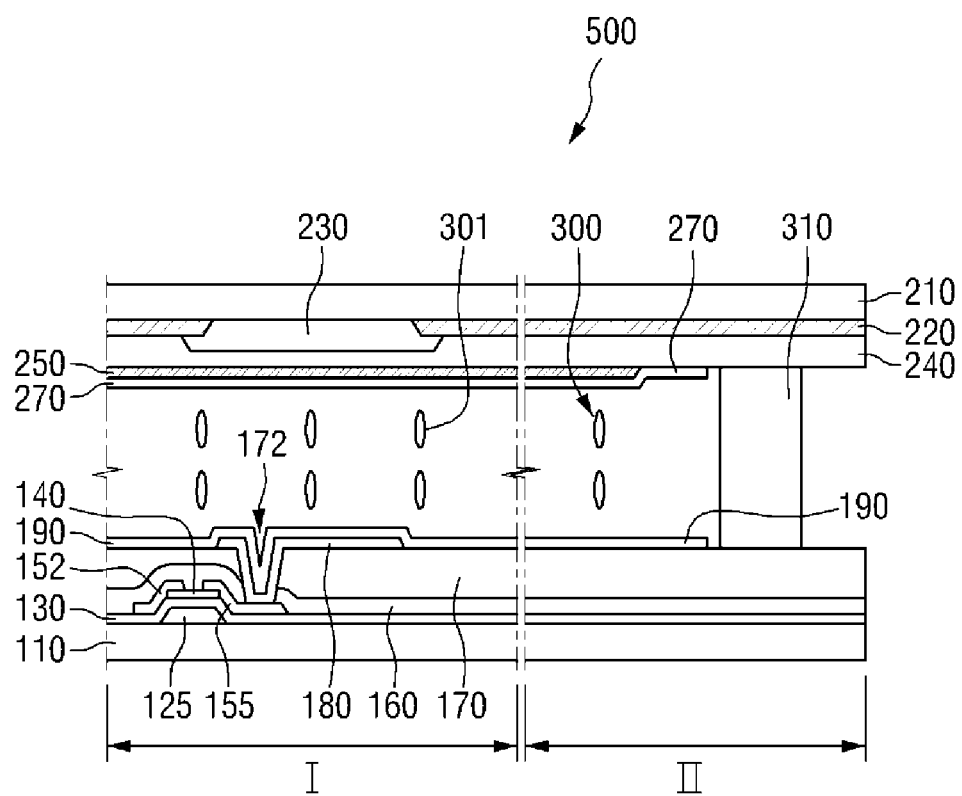
FIG. 2 is a schematic cross-sectional view of the exemplary LCD of FIG. 1.

FIG. 1 is a schematic exploded perspective view of an exemplary embodiment of a liquid crystal display 500. FIG. 2 is a schematic cross-sectional view of the LCD 500 of FIG. 1.

Referring to FIGS. 1 and 2, the LCD 500 may include a first display substrate 100, a second display substrate 200, which is spaced from, and faces, the first display substrate 100, and a liquid crystal layer 300, which is interposed between the first and second display substrates 100 and 200. Each of the first and second display substrates 100 and 200 includes a display area I and a non-display area II. In the display area I, a plurality of pixels PX, which are arranged in a matrix form, may be defined.

In the display area I of the first display substrate 100, a plurality of gate lines GL, which extend in a first direction, and a plurality of data lines DL, which extend in a second direction that is perpendicular to the first direction, may be formed. A pixel electrode 180 may be disposed in each of the pixels PX, which are defined by the gate lines GL and the data lines DL.

The pixel electrode 180 may be provided with a data voltage via a thin-film transistor (TFT), which is a switching device. A gate electrode 125, which is the control terminal of the TFT, may be connected to a gate line GL, a source electrode 152, which is the input terminal of the TFT, may be connected to a data line DL, and a drain electrode 155, which is the output terminal of the TFT, may be electrically connected to the pixel electrode 180 via a contact hole 172.

A channel of the TFT may be formed in a semiconductor layer 140. The semiconductor layer 140 may be disposed to overlap the gate electrode 125. The source and drain electrodes 152 and 155 may be spaced a distance apart from each other with the semiconductor layer 140 interposed therebetween. The pixel electrode 180 may form an electric field with a common electrode 250 and may control the alignment direction of a liquid crystal compound 301 in the liquid crystal layer 300, which is interposed between the pixel electrode 180 and the common electrode 250.

The non-display area II may be an area surrounding the display area I. Driving units (not illustrated) providing a gate driving signal and a data driving signal to each of the pixels PX in the display area I may be disposed in the non-display area II of the first display substrate 100.

In the display area I of the second display substrate 200, a color filter 230 may be formed for each of the pixels PX. Examples of the color filter 230 include red R, green G, and blue B color filters. The red R, green G, and blue B color filters may be alternately arranged. A light-blocking pattern 220 may be disposed along a boundary between the color filter 230 and a neighboring color filter 230 and thus the light-blocking pattern 220 may be disposed in the display area I and the non-display area II of the second display substrate 200. The light-blocking pattern 220 may have a larger width in the non-display area II than a light-blocking pattern 220 disposed along the boundary between the color filter 230 and the neighboring color filter 230. The common electrode 250, which is formed in one continuous piece, may be disposed on the entire surface of the display area I regardless of the pixels PX.

The first and second display substrates 100 and 200 may be bonded together by a seal line 310, which is formed of a sealant. The seal line 310 may account for the periphery of the first and second display substrates 100 and 200 and may be disposed in the non-display area II. The seal line 310 is formed along the periphery of the display area I and thus surrounds the display area I. The seal line 310 bonds the first and second display substrates 100 and 200 together and also defines a predetermined space therebetween. The liquid crystal layer 300 is inserted in the space defined by the seal line 310, and thus the seal line 310 may prevent the liquid crystal compound 301 from leaking.

The LCD 500 will hereinafter be described in detail. The first display substrate 100 may have a first substrate 110 as a base substrate. The first substrate 110 may include the display area I and the non-display area II. The first substrate 110 may be provided as a transparent insulating substrate formed of glass or a transparent plastic material.

The gate line GL, which is formed of a conductive material, and the gate electrode 125, which protrudes from the gate line GL, may be disposed on the first substrate 110 in the display area I. Although not specifically illustrated, the gate line GL may extend into the non-display area II and may form a gate pad (not illustrated) in the non-display area II. The gate line GL and the gate electrode 125 may be covered by a gate insulating layer 130. The gate insulating layer 130 may also be formed in the non-display area II.

The semiconductor layer 140 and an ohmic contact layer (not illustrated) may be formed on the gate insulating layer 130 in the display area I. The source electrode 152, which is branched off from the data line DL, and the drain electrode 155, which is spaced from the source electrode 152, may be formed on the semiconductor layer 140 and the ohmic contact layer. Although not specifically illustrated, the data line DL may extend into the non-display area II and may form a data pad (not illustrated) in the non-display area II.

A passivation layer 160, which is a type of insulating layer, may be formed on the source and drain electrodes 152 and 155, and an organic layer 170 may be formed on the passivation layer 160 using an organic material. The passivation layer 160 may be formed of an insulating material, such as a silicon nitride layer, a silicon oxide layer, or a silicon oxynitride layer. The passivation layer 160 and the organic layer 170 may be formed in the display area I and in the non-display area II. Optionally, the passivation layer 160 may not be present.

The pixel electrode 180 may be formed on the organic layer 170 in the display area I for each of the pixels PX, and may be formed using a conductive material. The pixel electrode 180 may be electrically connected to the drain electrode 155 via a contact hole 172 defined in the organic layer 170 and the passivation layer 160 and which exposes the drain electrode 155 therethrough. The pixel electrode 180 may be formed of at least one of indium tin oxide (ITO), indium zinc oxide (IZO), indium oxide, zinc oxide, tin oxide, gallium oxide, titanium oxide, aluminum (Al), silver (Ag), platinum (Pt), chromium (Cr), molybdenum (Mo), tantalum (Ta), niobium (Nb), zinc (Zn), magnesium (Mg), an alloy thereof, and a deposition layer thereof.

The second display substrate 200 will hereinafter be described. The second display substrate 200 has a second substrate 210 as a base substrate. The second substrate 210 may be provided as a transparent insulating substrate formed of glass or a transparent plastic material.

The light-blocking pattern 220 is formed on the second substrate 210. The light-blocking pattern 220 may be formed in the display area I and in the non-display area II. The color filter 230 may be formed on the light-blocking pattern 220 in the display area I. An overcoat layer 240 may be formed on the color filter 230 and the light-blocking pattern 220. The overcoat layer 240 may be formed in the display area I and in the non-display area II.

The common electrode 250 may be disposed on the overcoat layer 240. The common electrode 250 may be formed of at least one of ITO, IZO, indium oxide, zinc oxide, tin oxide, gallium oxide, titanium oxide, Al, Ag, Pt, Cr, Mo, Ta, Nb, Zn, Mg, an alloy thereof, and deposition layer thereof.

The common electrode 250 may be formed to cover the entire display area I. The common electrode 250 may include slits (not illustrated) or openings (not illustrated) in the display area I. The common electrode 250 may also be formed in the non-display area II, however, the common electrode 250 is not formed along, or near, the edges of the second display substrate 200, so that the overcoat layer 240 may be exposed. The pixel electrode 180 of the first display substrate 100 and the common electrode 250 of the second display substrate 200 may be disposed to face each other and may form an electric field in the liquid crystal layer 300.

The first and second display substrates 100 and 200 may be disposed to face each other while maintaining a predetermined cell gap therebetween. The liquid crystal layer 300 may be interposed between the first and second display substrates 100 and 200 in the display area I.

A liquid crystal alignment layer 190 may be formed on the first display substrate 100 and liquid a crystal alignment layer 270 may be formed on the second display substrate 200. The liquid crystal alignment layer 190 may be disposed between the first display substrate 100 and the liquid crystal layer 300 and between the first display substrate 100 and the seal line 310. The liquid crystal alignment layer 270 may be disposed between the second display substrate 200 and the liquid crystal layer 300 and between the second display substrate 200 and the seal line 310. In a non-limiting example, the liquid crystal alignment layers 190 and 270 may be polyimide-based liquid crystal alignment layers.

FIGS. 1 and 2 illustrate a color filter array in which the second display substrate 200 includes the color filter 230. Alternatively, the color filter 230 may be included in the first display substrate 100, in which case, the first display substrate 100 has a color filter-on-array (COA) structure in which a color filter is formed on a transparent insulating substrate where a TFT is formed.

Although not specifically illustrated, the LCD 500 may also include a backlight unit (not illustrated), which is disposed below the first display substrate 100, and an upper polarizing plate (not illustrated), which is disposed on the second display substrate 200.

The backlight unit may include, for example, a light guide plate (LGP), a light source unit, a reflection member, and one or more optical sheets.

The LGP changes the path of light generated by the light source unit so the light travels toward the liquid crystal layer 300. The LGP may include an incidence surface, which receives the light generated by the light source unit, and an emission surface, which faces the liquid crystal layer 300. The LGP may be formed of a material having a uniform refractive index, such as poly(methyl methacrylate) (PMMA) or polycarbonate (PC), but is not limited thereto. Light incident upon one or both sides of the LGP having a smaller incidence angle than the critical angle of the LGP, may thus enter the LGP. On the other hand, light incident upon the top or bottom surface of the LGP having a greater incidence angle than the critical angle of the LGP, may thus be evenly distributed throughout the LGP instead of being emitted out of the LGP.

A diffusion pattern may be formed on one of the top and bottom surfaces of the LGP to enable guided light to be emitted upwards. For example, the diffusion pattern may be formed on the bottom surface of the LGP that is opposite to the emission surface of the LGP. More specifically, in order for light transmitted within the LGP to be emitted upward, the diffusion pattern may be printed on one surface of the LGP with ink, but is not limited thereto. That is, the diffusion pattern may also be an array of fine grooves or protrusions formed on the surface of the LGP. Alternatively, various other modifications may be made to the diffusion pattern without departing from the scope of the invention.

The reflective member (not illustrated) may be additionally provided between the LGP and a lower receiving member (not illustrated). The reflective member reflects light emitted from the bottom surface of the LGP, which is opposite to, and faces, the emission surface of the LGP, and thus applies the light back to the LGP. The reflective member may be formed as a film, but is not limited thereto.

The light source unit may be disposed to face the incidence surface of the LGP. The number of light source units provided may be appropriately varied. In one exemplary embodiment, only one light source unit may be provided on one side of the LGP. In another exemplary embodiment, three or more light source units may be provided to correspond to three or more sides of the LGP. In yet another exemplary embodiment, a plurality of light source units may be provided to correspond to only one side of the LGP.

The backlight unit has been described above, taking as an example a side light-type backlight unit in which one or more light source units are provided on one or more sides of an LGP, but is not limited thereto. That is, the invention is also applicable to a direct-type backlight unit or another light source device, such as a surface-type light source device.

The light source unit may include a white light-emitting diode (LED), which emits white light, or a plurality of LEDs, which emit red (R) light, green (G) light and blue (B) light. In response to the light source unit including a plurality of LEDs, which emit R light, G light, and B light, white light may be realized by turning on all the LEDs to mix the R light, G light, and B light together.

The liquid crystal layer 300 will hereinafter be described in detail. The liquid crystal layer 300 may comprise at least one first compound represented by Formula 1:

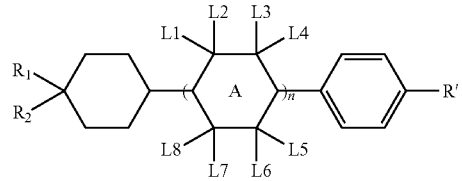
(Formula I)

where each of L1 to L8 is a hydrogen (H) or a fluorine (F);

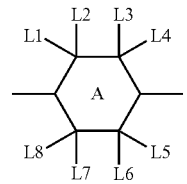

is a cyclohexyl group, a phenyl group, tetrahydropyran, 1,3-dioxane, a fluorocyclohexyl group, a fluorophenyl group, fluorotetrahydropyran, or fluoro-1,3-dioxane, each of $R_1$ and $R_2$ is independently a $C_{1-2}$ alkyl group; and R' is hydrogen, a $C_{1-5}$ alkyl group, a $C_{2-5}$ alkenyl group, or a $C_{1-5}$ alkoxy group.

Referring to Formula I, n is 0 to 2. If n is greater than 2, the long axis of the liquid crystal compound increases, and as a result, the rotational viscosity of the liquid crystal compound increases considerably, which is undesirable. Accordingly, n may be 2 or less.

When n=2, each

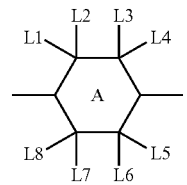

is independently a cyclohexyl group, a phenyl group, tetrahydropyran, 1,3-dioxane, a fluorocyclohexyl group, a fluorophenyl group, fluorotetrahydropyran, or fluoro-1,3-dioxane.

The first compound may be, but is not limited to, at least one of the compounds represented by Formulas I-1 through I-42:

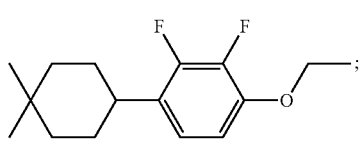
(Formula I-1)

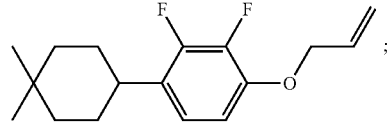
(Formula I-2)

-continued
(Formula I-3)
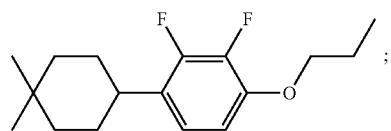
(Formula I-4)
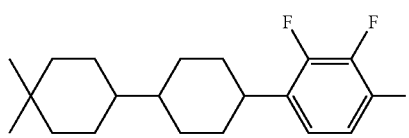
(Formula I-5)
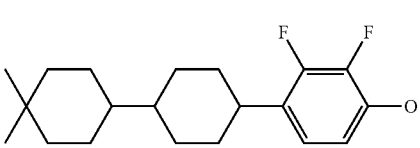
(Formula I-6)
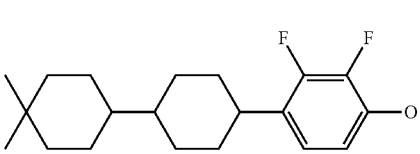
(Formula I-7)
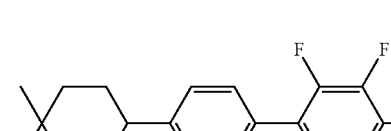
(Formula I-8)
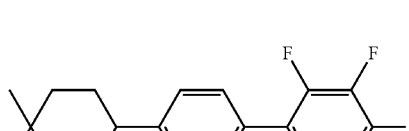
(Formula I-9)
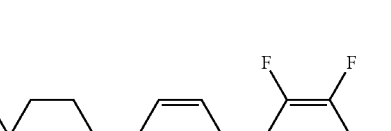
(Formula I-10)
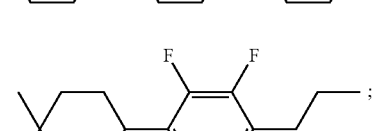
(Formula I-11)
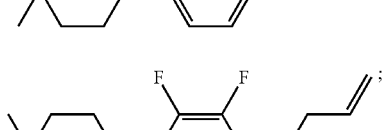
(Formula I-12)
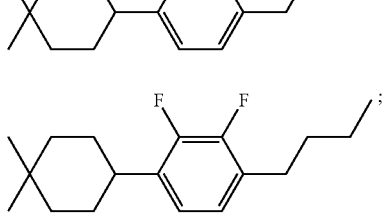
(Formula I-13)
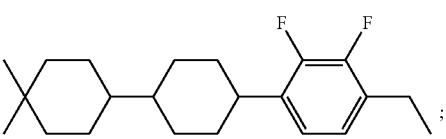
(Formula I-14)
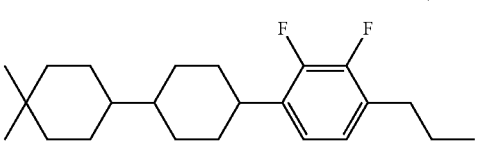
(Formula I-15)
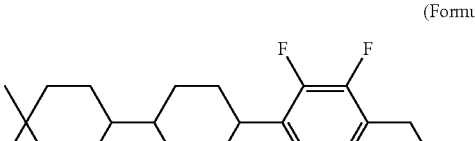
(Formula I-16)
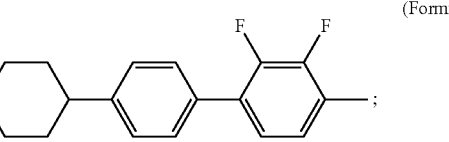
(Formula I-17)
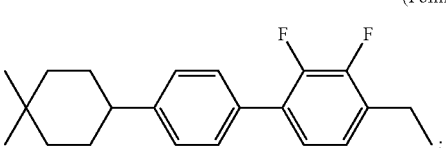
(Formula I-18)
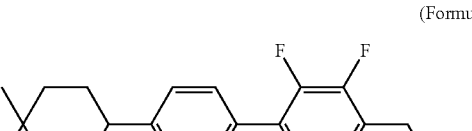
(Formula I-19)
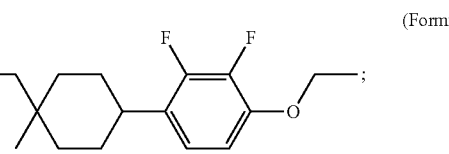
(Formula I-20)
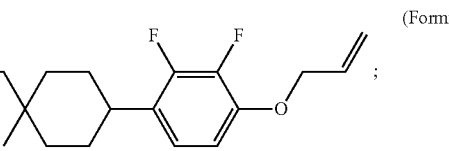
(Formula I-21)
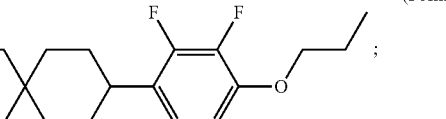
(Formula I-22)
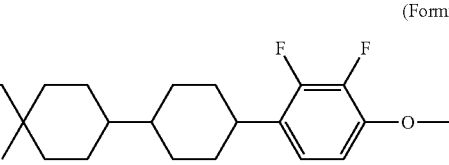

(Formula I-23)
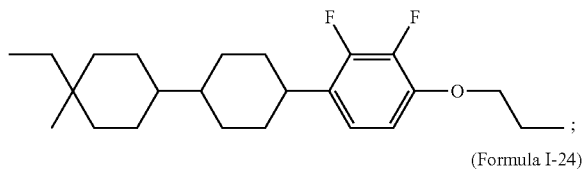
(Formula I-24)
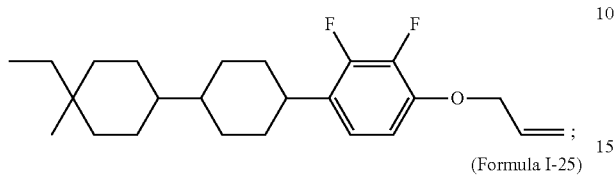
(Formula I-25)
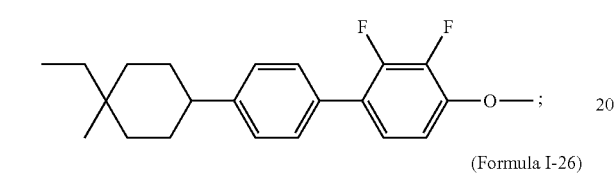
(Formula I-26)
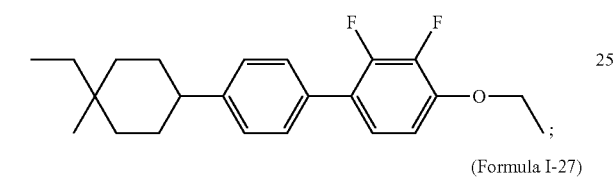
(Formula I-27)
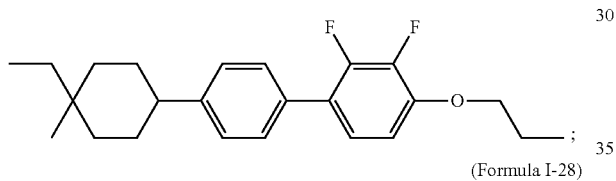
(Formula I-28)
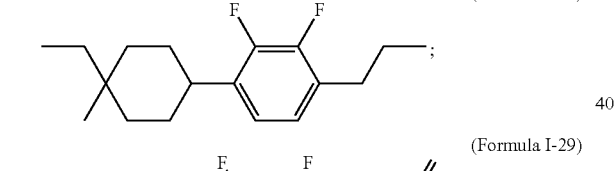
(Formula I-29)
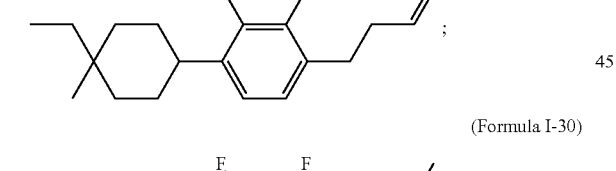
(Formula I-30)
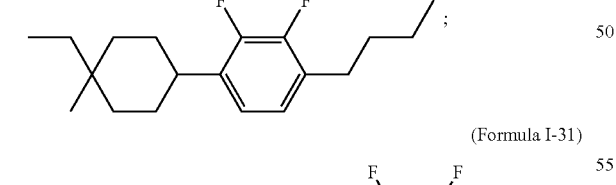
(Formula I-31)
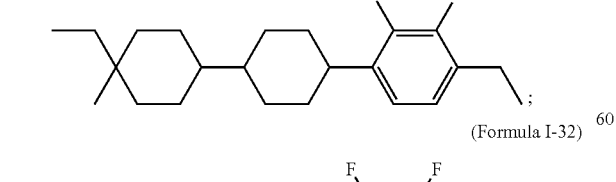
(Formula I-32)
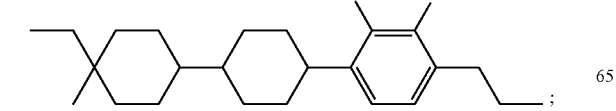
(Formula I-33)
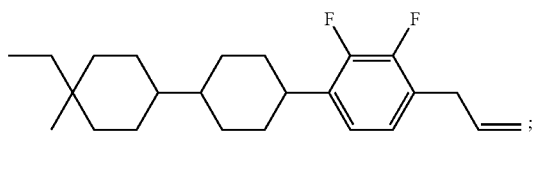
(Formula I-34)
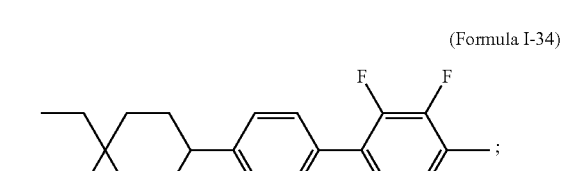
(Formula I-35)
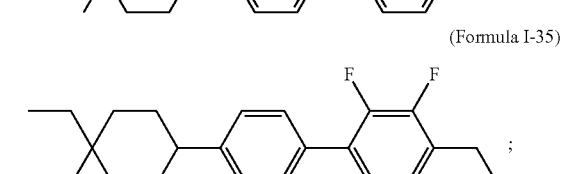
(Formula I-36)
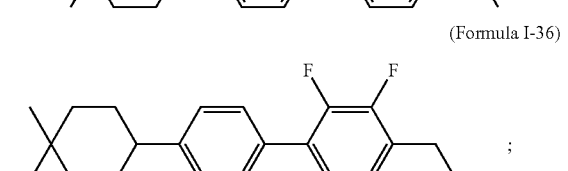
(Formula I-37)
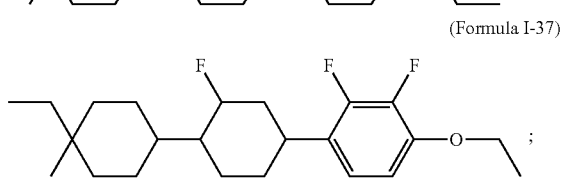
(Formula I-38)
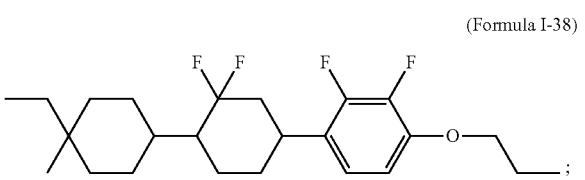
(Formula I-39)
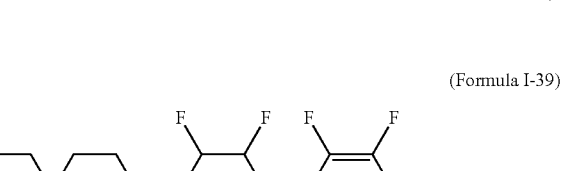
(Formula I-40)
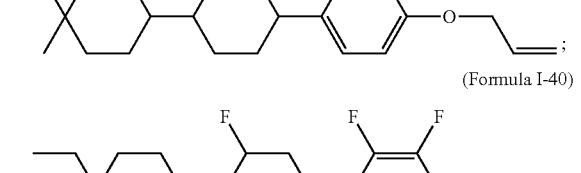
(Formula I-41)
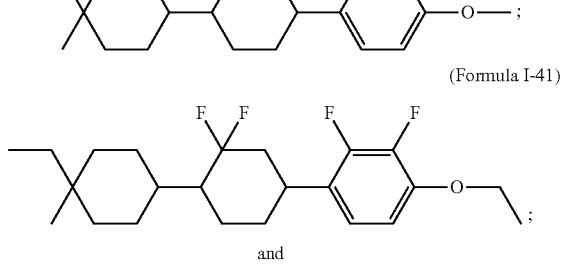
and (Formula I-42)

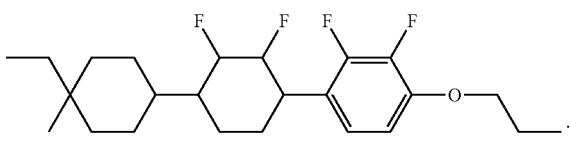

In a typical polar liquid crystal compound, at least one of the terminal groups on sides of a mesogen group is a $C_{3-5}$ alkyl group, a $C_{3-5}$ alkoxy group, or a $C_{3-5}$ alkenyl group. As the demand for a fast-response panel has increased, the demand for a low-viscosity liquid crystal compound has also increased. However, the greater the carbon number of the terminal groups of a liquid crystal compound, the higher the viscosity of the liquid crystal compound.

Since at least one of the terminal groups of the typical polar liquid crystal compound is a $C_{3-5}$ alkyl group, a $C_{3-5}$ alkoxy group, or a $C_{3-5}$ alkenyl group, the length of the long axis of the typical polar liquid crystal compound increases, and thus, the typical polar liquid crystal compound has a higher rotational viscosity than the first compound described herein.

Individual structural groups of a liquid crystal compound will hereinafter be referred to in the abbreviated forms shown in Table 1 below.

TABLE 1

| Structure | Abbreviation |
|---|---|
| 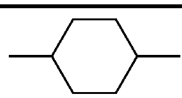 | C |
| 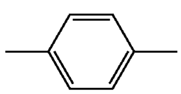 | P |
| 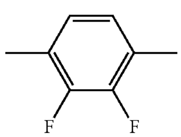 | A |
| 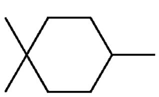 | T |
| 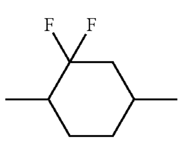 | B |
| 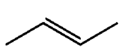 | V |
| 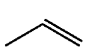 | V1 |
| —O— | O |
| 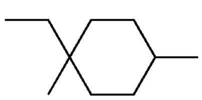 | T1 |

TABLE 1-continued

| Structure | Abbreviation |
|---|---|
| 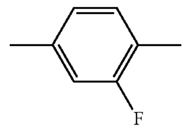 | L |

Tables 2 and 3 below show molecular weight (grams per mole; g/mol), dipole moment (D), dielectric anisotropy ($\Delta\epsilon$), rotational viscosity ($\gamma1$)(millipascal second; mPa·s), and low-temperature stability measurements for a typical polar liquid crystal molecule having a structure represented by Formula A (Table 2) and for an exemplary first compound represented by Formula I-8 (Table 3).

TABLE 2

| Classification | |
|---|---|
| (Formula A_3CPAO2) | |
| Molecular Weight (g/mol) | 358.47 |
| Dipole Moment (D) | 3.41 |
| Dielectric anisotropy ($\Delta\epsilon$) | −5.8 |
| Rotational Viscosity ($\gamma1$) (mPa · s) | 230 |
| Low-Temperature Stability | Average |

TABLE 3

| Classification | |
|---|---|
| (Formula I-8_TPAO2) | |
| Molecular Weight (g/mol) | 344.45 |
| Dipole Moment (D) | 3.41 |
| Dielectric anisotropy ($\Delta\epsilon$) | −5.7 |
| Rotational Viscosity ($\gamma1$)(mPa · s) | 150 |
| Low-Temperature Stability | Excellent |

Referring to Tables 2 and 3 above, the polar liquid crystal compound of Formula I-8 has almost the same level of dielectric anisotropy as the typical polar liquid crystal compound of Formula A, but has much better rotational viscosity and low-temperature stability than the typical polar liquid crystal compound of Formula A.

The liquid crystal layer 300 may further comprise at least one second compound represented by Formulas II-1 to II-8:

(Formula II-1)

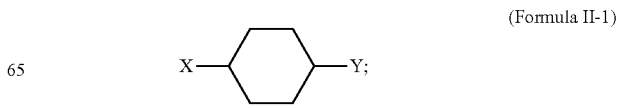

-continued

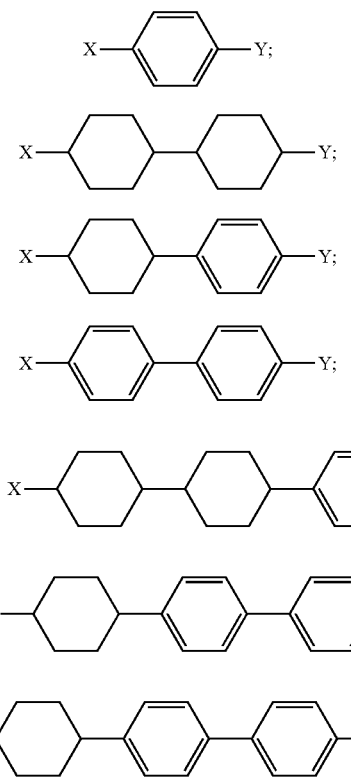

(Formula II-2)
(Formula II-3)
(Formula II-4)
(Formula II-5)
(Formula II-6)
(Formula II-7)

and (Formula II-8)

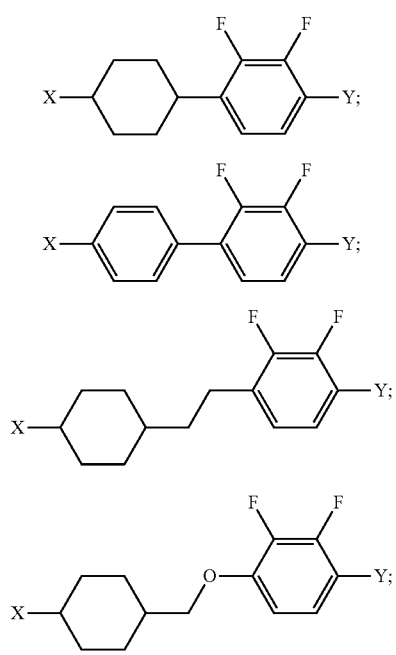

Where each X and Y are independently H, a $C_{1\sim5}$ alkyl group, a $C_{2\sim5}$ alkenyl group, a $C_{1\sim5}$ alkoxy group, a $C_{1\sim5}$ fluoroalkyl group, a $C_{2\sim5}$ fluoroalkenyl group, or a $C_{1\sim5}$ fluoroalkoxy group.

The liquid crystal layer 300 may further comprise at least one third compound represented by Formulas III-1 to III-12:

(Formula III-1)
(Formula III-2)
(Formula III-3)
(Formula III-4)
(Formula III-5)
(Formula III-6)
(Formula III-7)
(Formula III-8)
(Formula III-9)
(Formula III-10)
(Formula III-11)

and (Formula III-12)

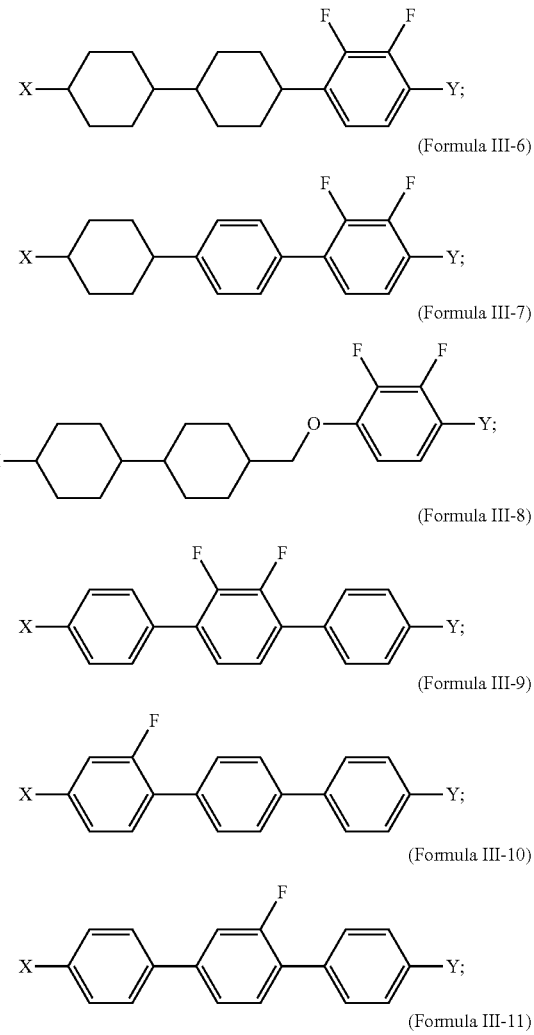

Where each X and Y are independently H, a $C_{1\sim6}$ alkyl group, a $C_{2\sim6}$ alkenyl group, a $C_{1\sim6}$ alkoxy group, a $C_{1\sim6}$ fluoroalkyl group, a $C_{2\sim6}$ fluoroalkenyl group, or a $C_{1\sim6}$ fluoroalkoxy group.

Tables 4 and 5 below show performance evaluation results for a liquid crystal composition including the liquid crystal compound of Formula A (Comparative Example) and for a liquid crystal composition including the exemplary first compound of Formula I-8 (Example).

TABLE 4
| Liquid Crystal Composition (Comparative Example) | Content (Wt %) | Performance Evaluation |
|---|---|---|
| 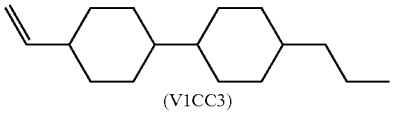 (V1CC3) | 20 | VHR (UV 5J): 88.5%<br>Δn(ne-no): 0.095<br>Δε($\epsilon_\parallel - \epsilon_\perp$): −4.9<br>γ1: 160 mPa · s |
| 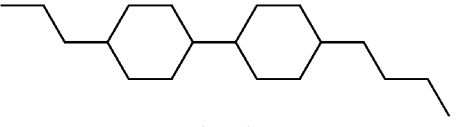 (3CC4) | 14 | |
| 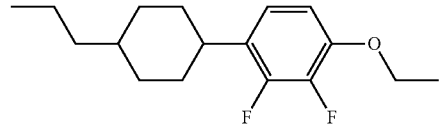 (3CAO2) | 22 | |
| 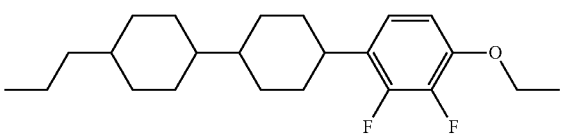 (3CCAO2) | 22 | |
| 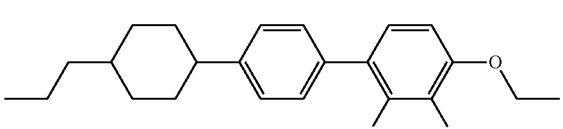 (3CPAO2) | 22 | |
TABLE 5
| Liquid Crystal Composition (Example) | Content (Wt %) | Performance Evaluation |
|---|---|---|
| 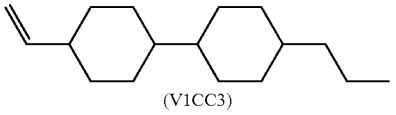 (V1CC3) | 20 | VHR (UV 5J): 88.4%<br>Δn(ne-no): 0.092<br>Δε($\epsilon_\parallel - \epsilon_\perp$): −4.8<br>γ1: 152 mPa · s |
| 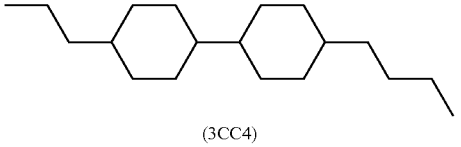 (3CC4) | 14 | |
| 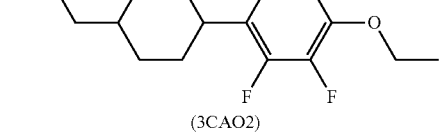 (3CAO2) | 22 | |
| 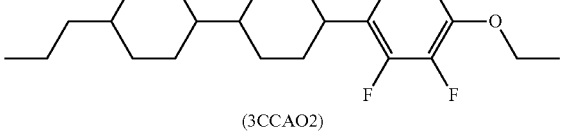 (3CCAO2) | 22 | |

TABLE 5-continued

| Liquid Crystal Composition (Example) | Content (Wt %) | Performance Evaluation |
|---|---|---|
| 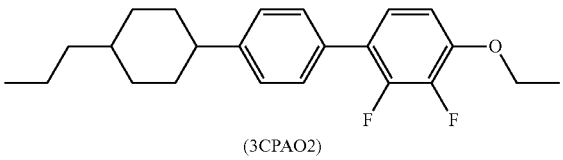 (3CPAO2) | 12 | |
| 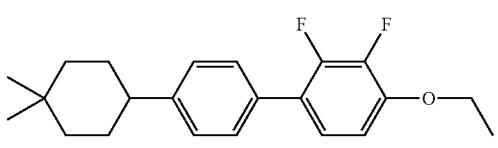 [SMILES: CCOc1ccc(-c2ccc(C3CCC(C)(C)CC3)cc2)c(F)c1F] (TPAO2) | 10 | |

Referring to Tables 4 and 5 above, the Example liquid crystal composition has almost the same physical properties as the Comparative Example liquid crystal composition and yet has a better, or at least equivalent, rotational viscosity, reliability, and low-temperature stability than the liquid crystal composition of the Comparative Example.

While the present disclosure has been particularly shown and described with reference to exemplary embodiments thereof, it will be understood by those of ordinary skill in the art that various changes in implementation and detail may be made therein without departing from the spirit and scope of the following claims. The exemplary embodiments should be considered in a descriptive sense only and not for purposes of limitation.

What is claimed is:

1. A liquid crystal composition, comprising:
at least one first compound represented by Formula I:

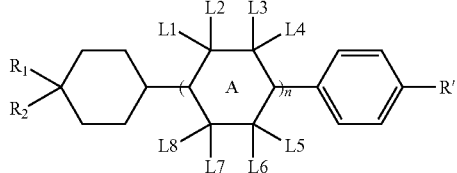

(Formula I)

wherein
each of L1 to L8 is a hydrogen or a fluorine;

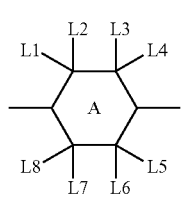

is a cyclohexyl group, a phenyl group, tetrahydropyran, 1,3-dioxane, a fluorocyclohexyl group, a fluorophenyl group, fluorotetrahydropyran, or fluoro-1,3-dioxane;

n is 0 to 2, and when n=2, each

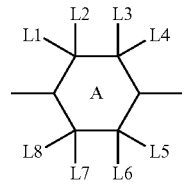

is independently a cyclohexyl group, a phenyl group, tetrahydropyran, 1,3-dioxane, a fluorocyclohexyl group, a fluorophenyl group, fluorotetrahydropyran, or fluoro-1,3-dioxane;

each of $R_1$ and $R_2$ are independently a $C_{1-2}$ alkyl group; and

R' is hydrogen, a $C_{1-5}$ alkyl group, a $C_{2-5}$ alkenyl group, or a $C_{1-5}$ alkoxy group.

2. The liquid crystal composition of claim 1, wherein the first compound is at least one of compounds represented by Formulas I-1 to I-42:

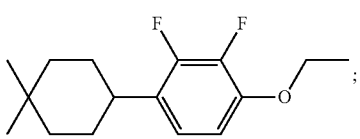

(Formula I-1)

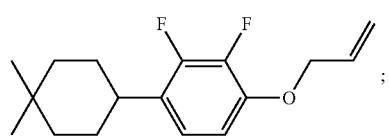

(Formula I-2)

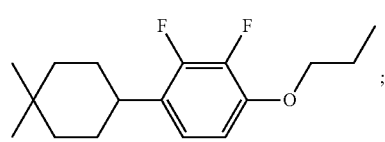

(Formula I-3)

(Formula I-4)
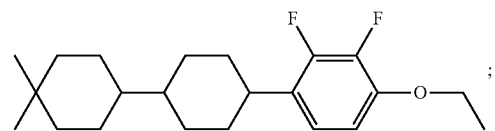
(Formula I-5)
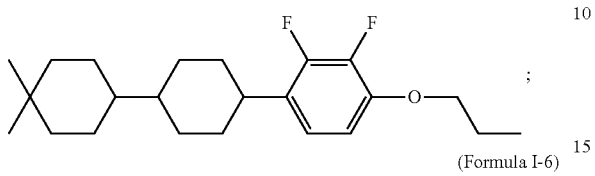
(Formula I-6)
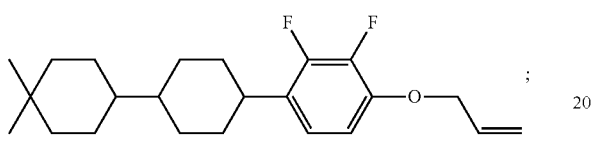
(Formula I-7)
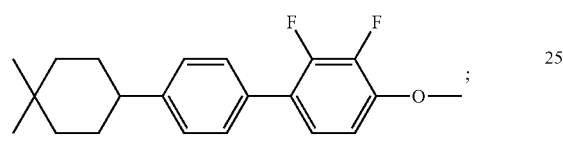
(Formula I-8)
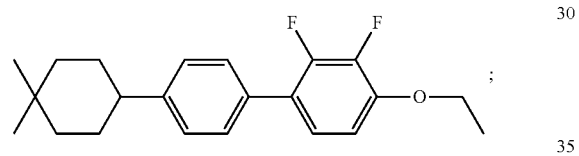
(Formula I-9)
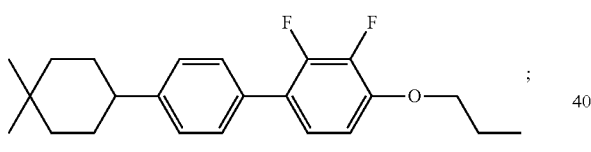
(Formula I-10)
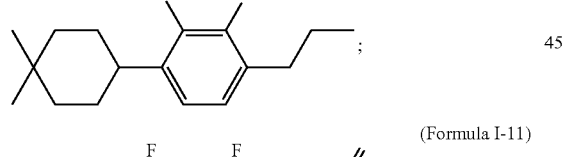
(Formula I-11)
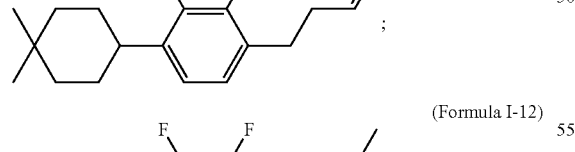
(Formula I-12)
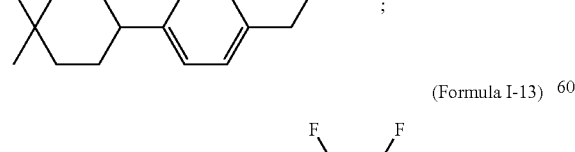
(Formula I-13)
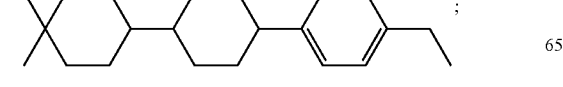
(Formula I-14)
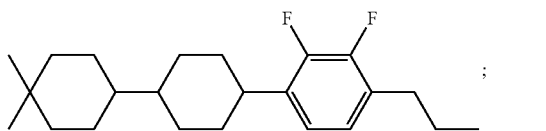
(Formula I-15)
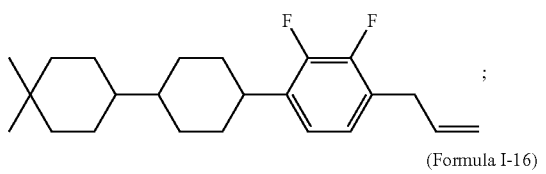
(Formula I-16)
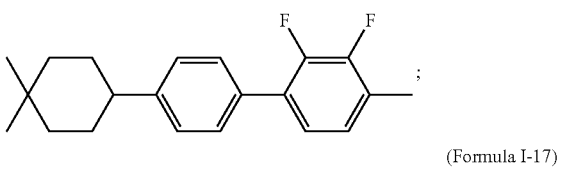
(Formula I-17)
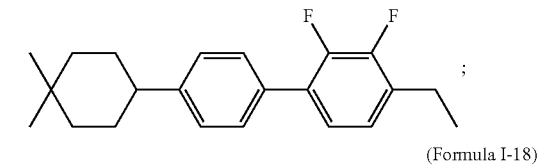
(Formula I-18)
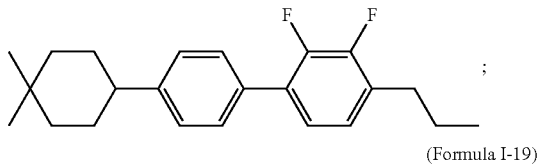
(Formula I-19)
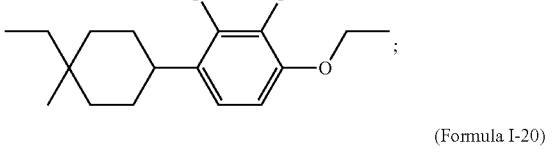
(Formula I-20)
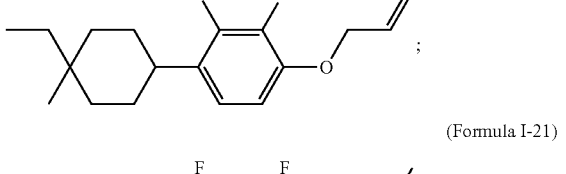
(Formula I-21)
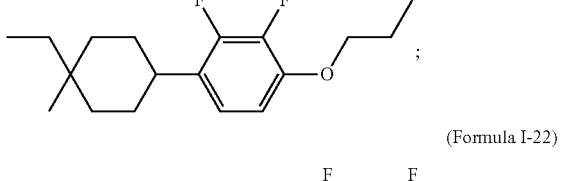
(Formula I-22)
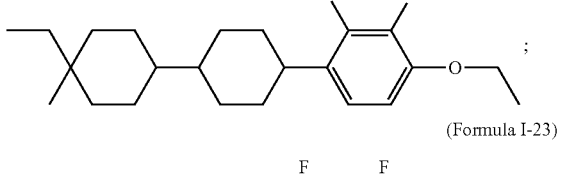
(Formula I-23)
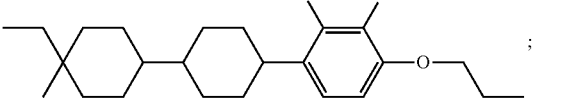

(Formula I-24)
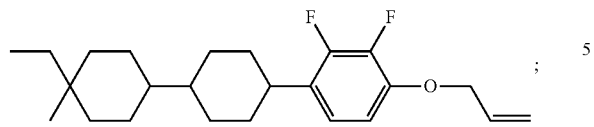
(Formula I-25)
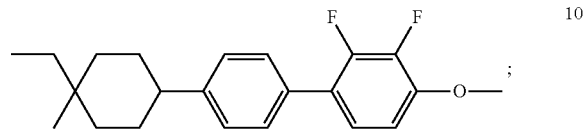
(Formula I-26)
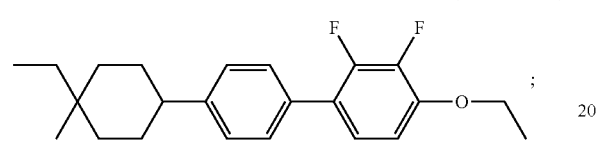
(Formula I-27)
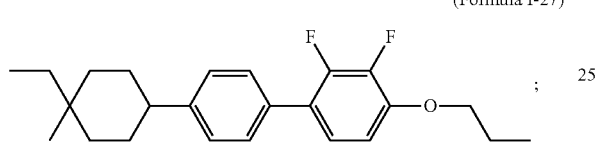
(Formula I-28)
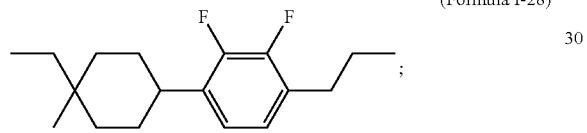
(Formula I-29)
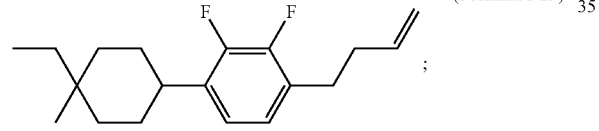
(Formula I-30)
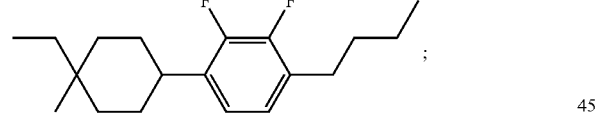
(Formula I-31)
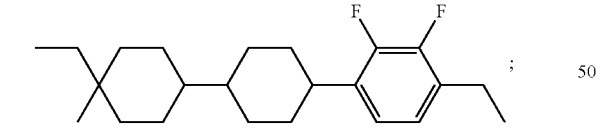
(Formula I-32)
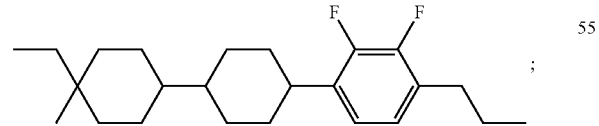
(Formula I-33)
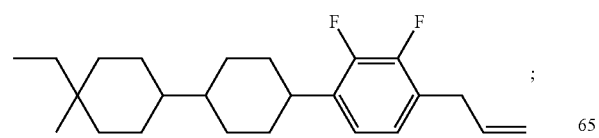
(Formula I-34)
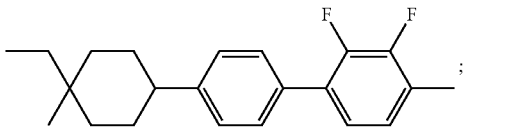
(Formula I-35)
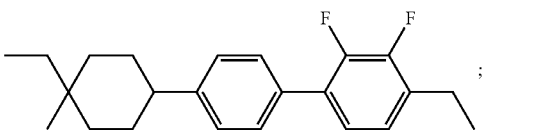
(Formula I-36)
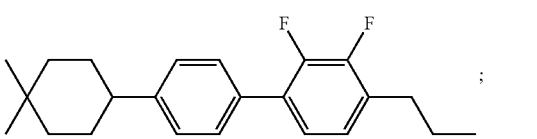
(Formula I-37)
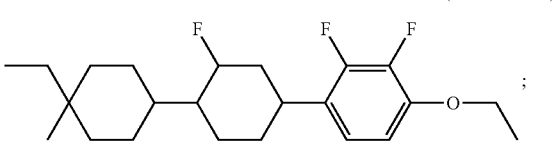
(Formula I-38)
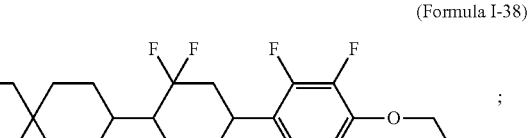
(Formula I-39)
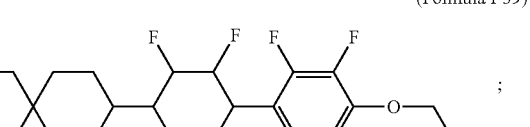
(Formula I-40)
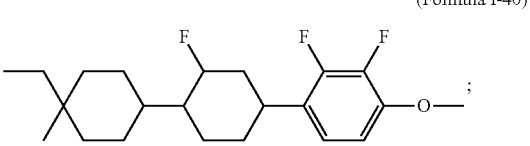
(Formula I-41)
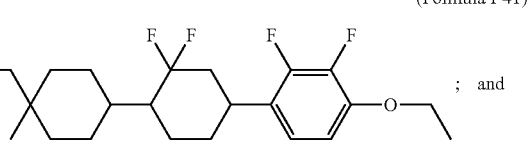
; and
(Formula I-42)
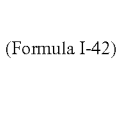
3. The liquid crystal composition of claim 1, further comprising at least one second compound represented by Formulas II-1 to II-8:

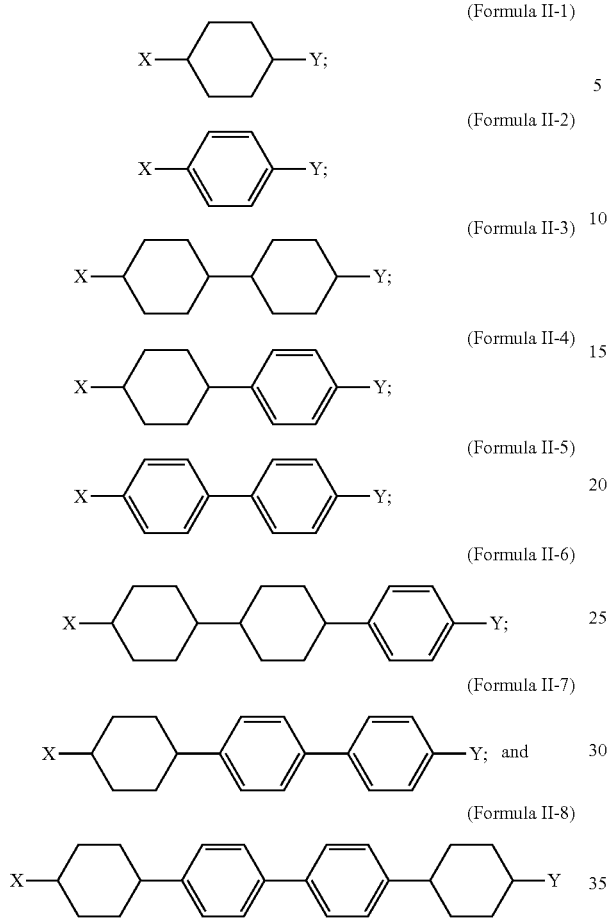

(Formula II-1)
(Formula II-2)
(Formula II-3)
(Formula II-4)
(Formula II-5)
(Formula II-6)
(Formula II-7)
(Formula II-8)

wherein each X and Y are independently hydrogen, a $C_{1\sim5}$ alkyl group, a $C_{2\sim5}$ alkenyl group, a $C_{1\sim5}$ alkoxy group, a $C_{1\sim5}$ fluoroalkyl group, a $C_{2\sim5}$ fluoroalkenyl group, or a $C_{1\sim5}$ fluoroalkoxy group.

4. The liquid crystal composition of claim 1, further comprising at least one third compound represented by Formulas III-1 to III-12:

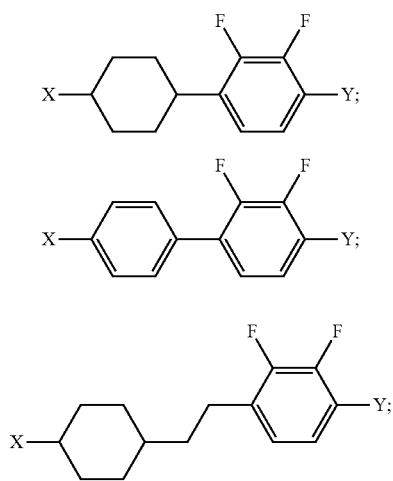

(Formula III-1)
(Formula III-2)
(Formula III-3)

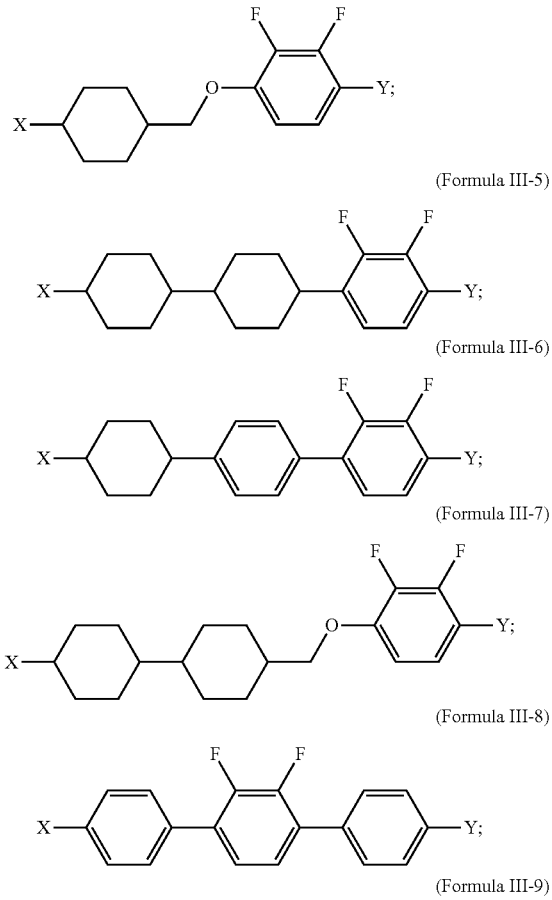

(Formula III-4)
(Formula III-5)
(Formula III-6)
(Formula III-7)
(Formula III-8)
(Formula III-9)
(Formula III-10)
(Formula III-11)

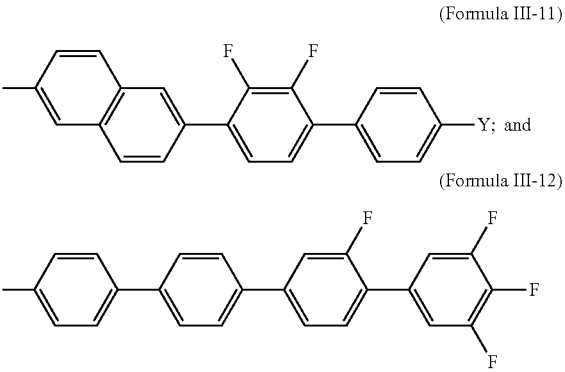

(Formula III-12)

wherein each X and Y are independently hydrogen, a $C_{1\sim6}$ alkyl group, a $C_{2\sim6}$ alkenyl group, a $C_{1\sim6}$ alkoxy group, a $C_{1\sim6}$ fluoroalkyl group, a $C_{2\sim6}$ fluoroalkenyl group, or a $C_{1\sim6}$ fluoroalkoxy group.

5. A liquid crystal display (LCD), comprising:

a first display substrate comprising one or more thin-film transistor (TFT);

a second display substrate facing the first display substrate; and a liquid crystal layer comprising at least one first compound represented by Formula I:

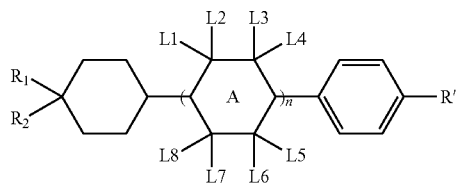
(Formula I)

wherein
each of L1 to L8 is a hydrogen or a fluorine;

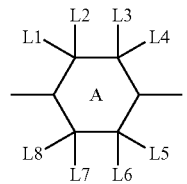

is a cyclohexyl group, a phenyl group, tetrahydropyran, 1,3-dioxane, a fluorocyclohexyl group, a fluorophenyl group, fluorotetrahydropyran, or fluoro-1,3-dioxane;

n is 0 to 2, and when n=2, each

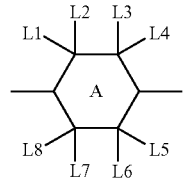

is independently a cyclohexyl group, a phenyl group, tetrahydropyran, 1,3-dioxane, a fluorocyclohexyl group, a fluorophenyl group, fluorotetrahydropyran, or fluoro-1,3-dioxane;

each of $R_1$ and $R_2$ are independently a $C_{1\sim2}$ alkyl group; and

R' is hydrogen, a $C_{1\sim5}$ alkyl group, a $C_{2\sim5}$ alkenyl group, or a $C_{1\sim5}$ alkoxy group.

6. The LCD of claim 5, wherein the first compound is at least one of compounds represented by Formulas I-1 to I-42:

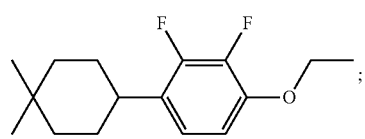
(Formula I-1)

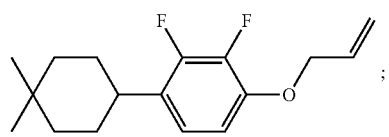
(Formula I-2)

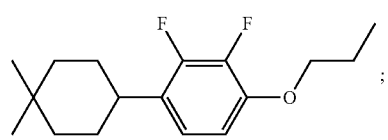
(Formula I-3)

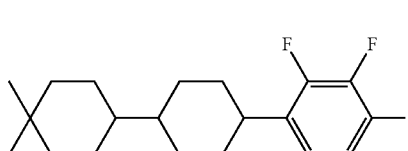
(Formula I-4)

(Formula I-5)

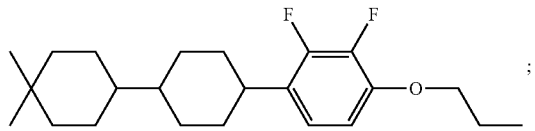
(Formula I-6)

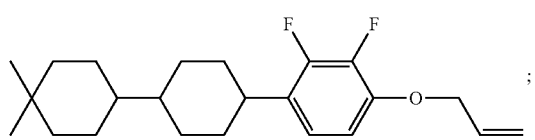
(Formula I-7)

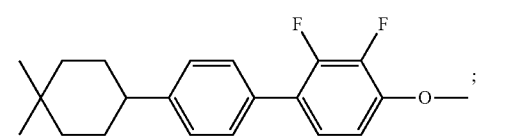
(Formula I-8)

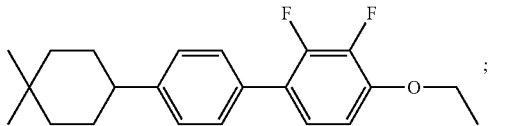
(Formula I-9)

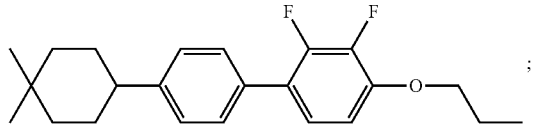
(Formula I-10)

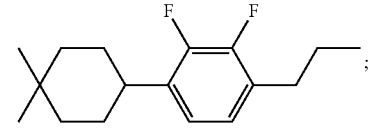
(Formula I-11)

(Formula I-12)
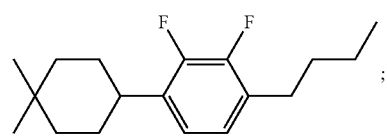
(Formula I-13)
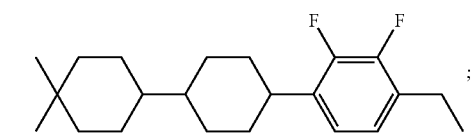
(Formula I-14)
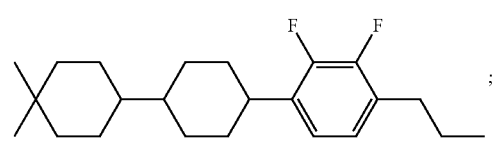
(Formula I-15)
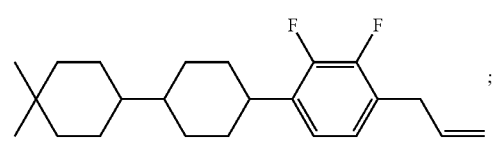
(Formula I-16)
(Formula I-17)
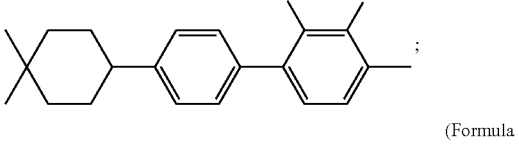
(Formula I-18)
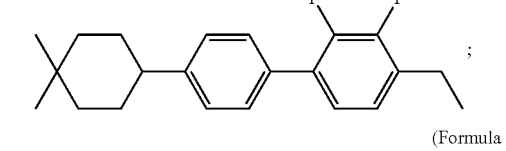
(Formula I-19)
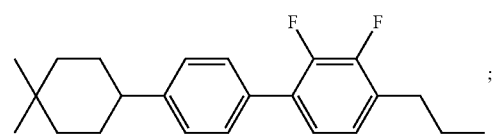
(Formula I-20)
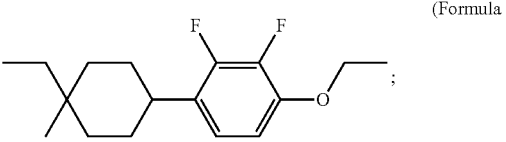
(Formula I-21)
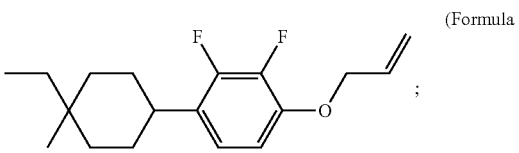
(Formula I-22)
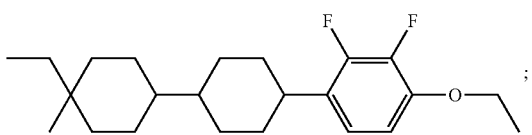
(Formula I-23)
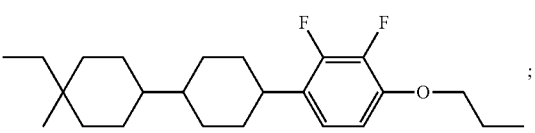
(Formula I-24)
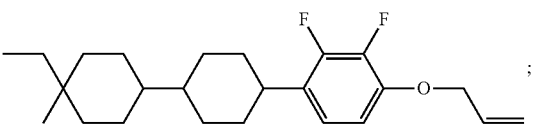
(Formula I-25)
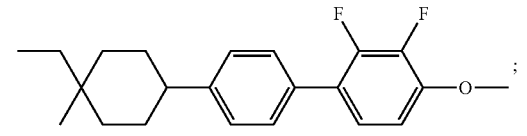
(Formula I-26)
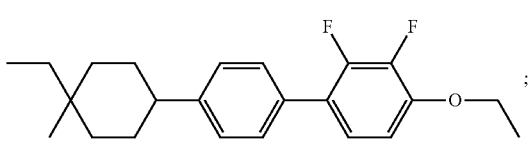
(Formula I-27)
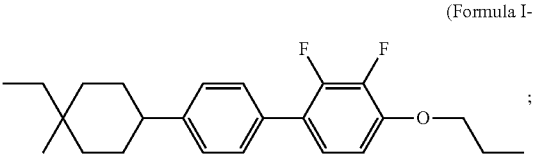
(Formula I-28)
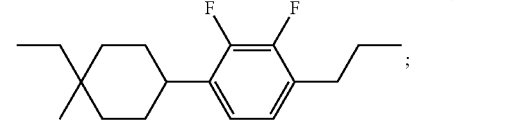
(Formula I-29)
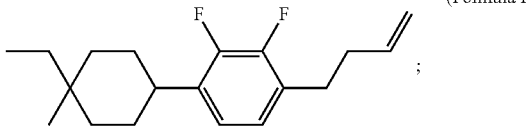
(Formula I-30)
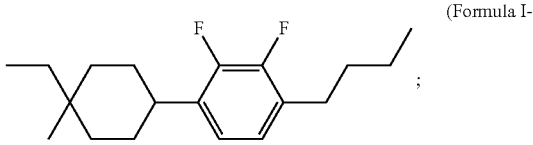
(Formula I-31)
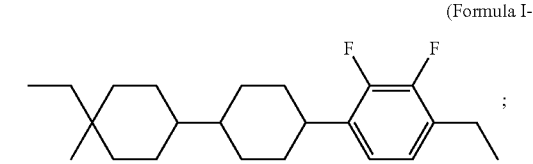

-continued

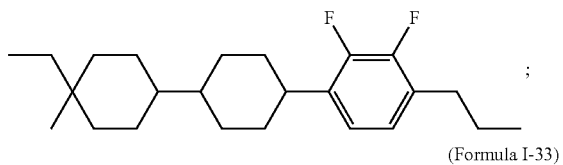
(Formula I-32)

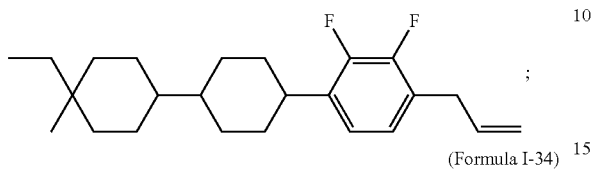
(Formula I-33)

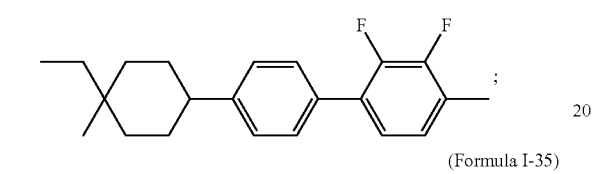
(Formula I-34)

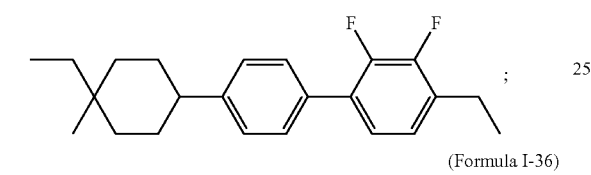
(Formula I-35)

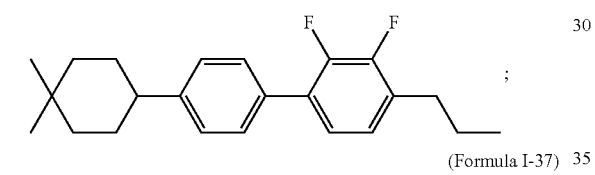
(Formula I-36)

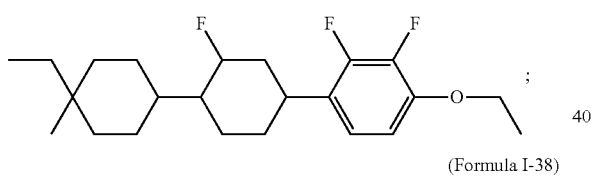
(Formula I-37)

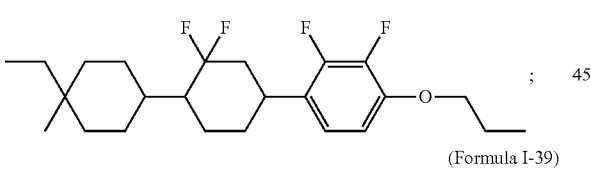
(Formula I-38)

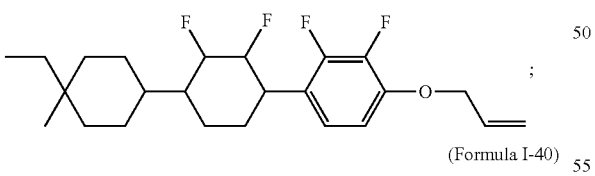
(Formula I-39)

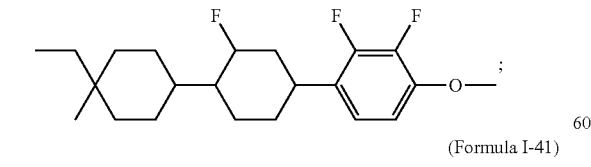
(Formula I-40)

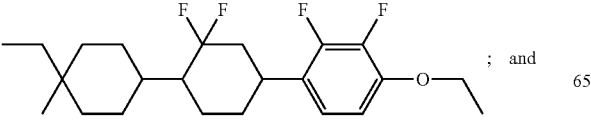
(Formula I-41)

-continued

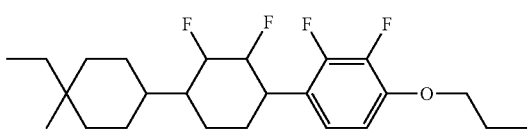
(Formula I-42)

7. The LCD of claim 5, wherein the liquid crystal layer further comprises at least one second compound represented by Formulas II-1 to II-8:

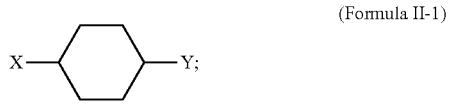
(Formula II-1)

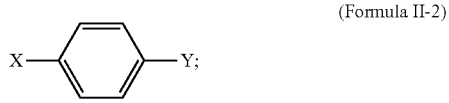
(Formula II-2)

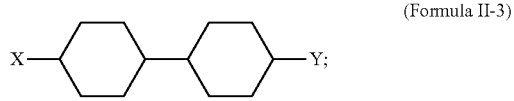
(Formula II-3)

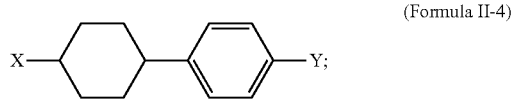
(Formula II-4)

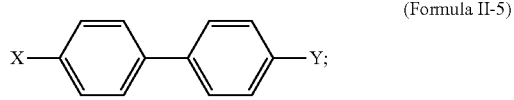
(Formula II-5)

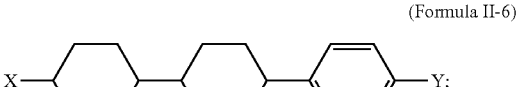
(Formula II-6)

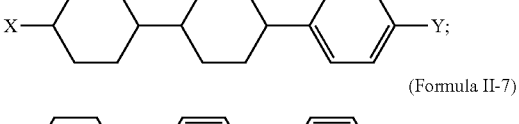
(Formula II-7)

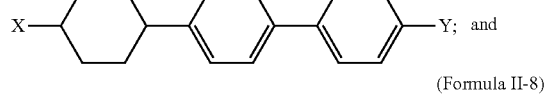
(Formula II-8)

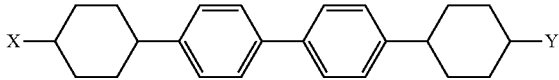

wherein each X and Y are independently hydrogen, a $C_{1\sim5}$ alkyl group, a $C_{2\sim5}$ alkenyl group, a $C_{1\sim5}$ alkoxy group, a $C_{1\sim5}$ fluoroalkyl group, a $C_{2\sim5}$ fluoroalkenyl group, or a $C_{1\sim5}$ fluoroalkoxy group.

8. The LCD of claim 5, wherein the liquid crystal layer further comprises at least one third compound represented by Formulas III-1 to III-12:

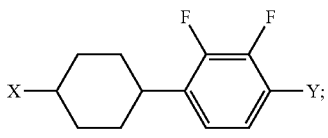
(Formula III-1)

-continued

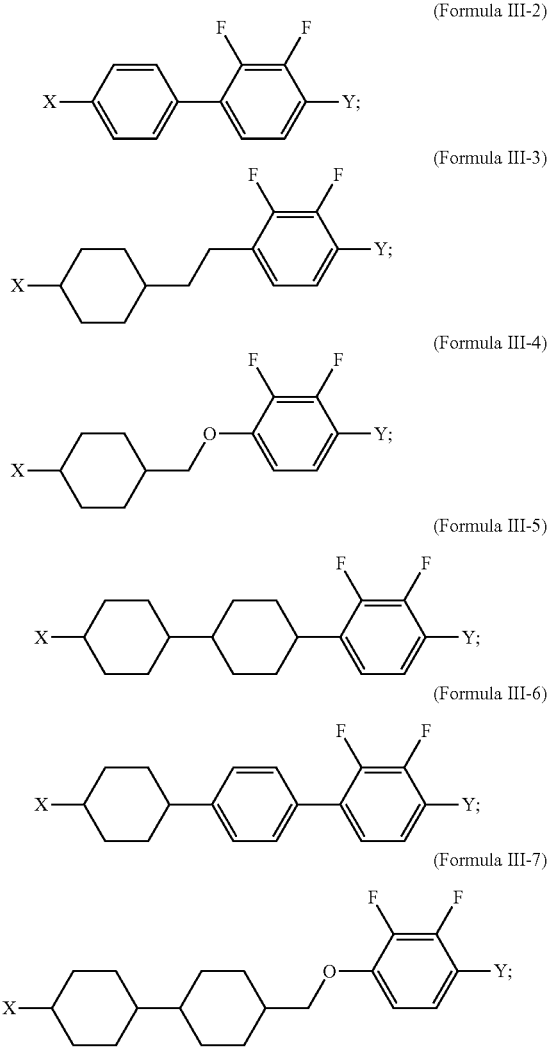

(Formula III-2)
(Formula III-3)
(Formula III-4)
(Formula III-5)
(Formula III-6)
(Formula III-7)

-continued

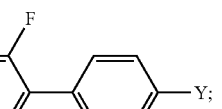
(Formula III-8)

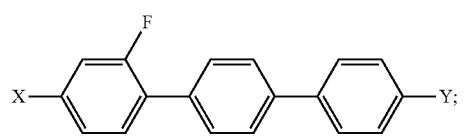
(Formula III-9)

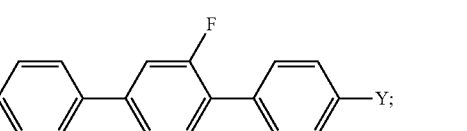
(Formula III-10)

(Formula III-11)

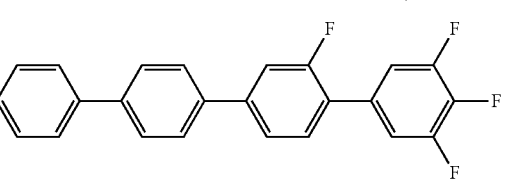
(Formula III-12)

wherein each X and Y are independently hydrogen, a $C_{1\sim6}$ alkyl group, a $C_{2\sim6}$ alkenyl group, a $C_{1\sim6}$ alkoxy group, a $C_{1\sim6}$ fluoroalkyl group, a $C_{2\sim6}$ fluoroalkenyl group, or a $C_{1\sim6}$ fluoroalkoxy group.

\* \* \* \* \*